(12) United States Patent
Yamaichi

(10) Patent No.: US 8,603,415 B2
(45) Date of Patent: Dec. 10, 2013

(54) MICROCHIP

(75) Inventor: Masato Yamaichi, Kyoto (JP)

(73) Assignee: Rohm Co., Ltd., Kyoto (JP)

( * ) Notice: Subject to any disclaimer, the term of this patent is extended or adjusted under 35 U.S.C. 154(b) by 398 days.

(21) Appl. No.: 12/644,259

(22) Filed: Dec. 22, 2009

(65) Prior Publication Data

US 2010/0196204 A1 Aug. 5, 2010

(30) Foreign Application Priority Data

Dec. 22, 2008 (JP) ................................. 2008-325064

(51) Int. Cl.
*G01N 33/48* (2006.01)
(52) U.S. Cl.
USPC ............. 422/506; 422/72; 422/255; 422/258; 422/503; 422/533; 422/548; 422/551; 422/554; 422/559; 494/22; 210/265; 210/513; 210/800
(58) Field of Classification Search
USPC ...................... 422/68.1, 72; 436/45
See application file for complete search history.

(56) References Cited

U.S. PATENT DOCUMENTS 4,788,154 A * 11/1988 Guigan .......................... 436/180

FOREIGN PATENT DOCUMENTS

JP 2007-033225 2/2007

* cited by examiner

*Primary Examiner* — Jill Warden
*Assistant Examiner* — Timothy G Kingan
(74) *Attorney, Agent, or Firm* — Fish & Richardson P.C.

(57) ABSTRACT

A microchip including a separation portion for separating a first component and a second component from a sample containing the first component and the second component, respectively, a first collection portion for collecting the first component, a second collection portion for collecting the second component, a first flow path for guiding the first component from the separation portion to the first collection portion, and a second flow path for guiding the second component from the separation portion to the second collection portion is provided.

8 Claims, 9 Drawing Sheets

MICROCHIP

BACKGROUND OF THE INVENTION

1. Field of the Invention

The present invention relates to a microchip useful for the purpose of µ-TAS (Micro Total Analysis System) suitably employed in biochemical tests such as of blood, in chemical synthesis, in environmental analysis, and the like.

2. Description of the Background Art

Recently, in the field of medical, health, food and drug discovery, there is greater importance of sensing, detecting, and determining the quantity of chemical substance and biological matters such as DNA (Deoxyribo Nucleic Acid), enzyme, antigen, antibody, protein, viruses and cells. Various biochips and microchemical chips (hereinafter, generically referred to as "microchip") have been proposed to enable feasible measurements.

For example, the microchip disclosed in Japanese Patent Laying-Open No. 2007-33225 includes a fluid circuit therein; constituted mainly of various portions such as a liquid reagent holding portion for holding a liquid reagent required to treat a sample (blood or the like) that is the target of testing/analysis, or for reaction with the sample; a quantification portion for quantifying the sample (or particular component in the sample) and/or the liquid reagent; a mixing portion mixing the sample (or particular component in the sample) with the liquid reagent; a detection portion for analyzing and/or examining the mixed liquid; and a minute flow path (for example, a width of approximately several hundred µm) appropriately connecting the portions.

Since such a microchip including a fluid circuit allows the series of experiments and analytical operations required to be carried out at a laboratory to be conducted within a chip of several centimeters in square and having a thickness of several millimeters, various advantages can be offered such as reduction in the amount of sample and reagent required, lower cost, faster reaction rate, and allowing testing with high throughput. Moreover, the test results of the sample can be obtained without delay at the site where the sample was collected. Microchips have been employed suitably for biochemical examination such as blood testing and the like.

SUMMARY OF THE INVENTION

A conventional microchip is disadvantageous in that, even if the blood is separated into blood cells and plasma by centrifugal operation, only one component of the blood, plasma for example, can be collected. Blood cells that are another component of blood could not be collected and measured at the same time. Therefore, in the case where the glucose level is to be examined to arrive at a diagnosis of diabetes, it is necessary to measure the amount of hemoglobin Alc (HbAlc) in the blood cell indicating the average glucose level over approximately three months in the past prior to the date of collecting the blood cell, and at the same time measure the amount of glucose in the blood plasma indicating the glucose level over several hours from the point of time of collecting the blood plasma.

In view of the foregoing, an object of the present invention is to provide a microchip allowing collection and quantification of a plurality of components in a specimen.

The present invention provides a microchip including a separation portion separating a first component and a second component from a specimen containing first and second components, a first collection portion collecting the first component, a second collection portion collecting the second component, a first flow path guiding the first component from the separation portion to the first collection portion, and a second flow path guiding the second component from the separation portion to the second collection portion.

In the microchip of the present invention, each of the first and second flow paths preferably extends in a direction radiating from the center of centrifugal force applied to the microchip.

In the microchip of the present invention, the separation portion preferably includes a first separation portion separating at least a portion of the first component from the specimen, a second separation portion separating at least a portion of the second component from the specimen, and a third flow path guiding a portion of the first component and the second component of the specimen from the first separation portion to the second separation portion. The first flow path is located between the first separation portion and the first collection portion, and the second flow path is located between the second separation portion and the second collection portion.

In the microchip of the present invention, the first flow path and the third flow path may be partially shared. Furthermore, the second flow path and the third flow path may be partially shared.

Furthermore, the present invention provides a microchip including a first separation portion separating at least a portion of a first component from a specimen containing first and second components, a second separation portion separating at least a portion of a second component from the specimen containing first and second components, and a flow path guiding a portion of the first component and the second component of the specimen from the first separation portion to the second separation portion. The first component is obtained by separating the first component from the first separation portion. The second component is obtained by separating the second component from the second separation portion.

The microchip of the present invention preferably includes a first collection portion collecting the first component, a second collection portion collecting the second component, a first flow path guiding the first component from the first separation portion to the first collection portion, and a second flow path guiding the second component from the second separation portion to the second collection portion.

In the microchip of the present invention, each of the first and second flow paths preferably extends in a direction radiating from the center of centrifugal force applied to the microchip.

In the microchip of the present invention, the second separation portion, the second collection portion, the first separation portion and the first collection portion are preferably arranged in the cited order on concentric circles differing in the direction radiating from the center of centrifugal force.

In the present specification, the recitation of "portion A and portion B are connected" includes the case where portion A and portion B are directly connected physically, as well as the case where portion A and portion B are connected indirectly via a minute flow path (small flow path) and/or various functional portions.

According to the microchip of the present invention, a fluid including at least two components such as blood can be completely divided into plasma and blood cells, and first and second components can be collected individually in synchronism with an operation that will be described afterwards. A plurality of predetermined items can be measured simultaneously through subsequent various processes.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS (First Embodiment)

In a microchip including an internal fluid circuit such as a microchip of the present invention, the series of operations such as the quantification of a specimen and liquid reagent, the mixing of the specimen and liquid reagent, the transfer of the specimen, the liquid reagent and mixed liquid to each site in the fluid circuit can be carried out by applying centrifugal force towards the microchip in an appropriate direction. Application of the centrifugal force towards the microchip is carried out employing a centrifuge device having a microchip mount portion for mounting a microchip. The rotary motion to apply centrifugal force to the microchip is called "orbital motion", whereas modifying the direction of the microchip to alter the direction of applying centrifugal force towards the microchip is referred to as a rotation movement turning on its own axis.

Figure 1:
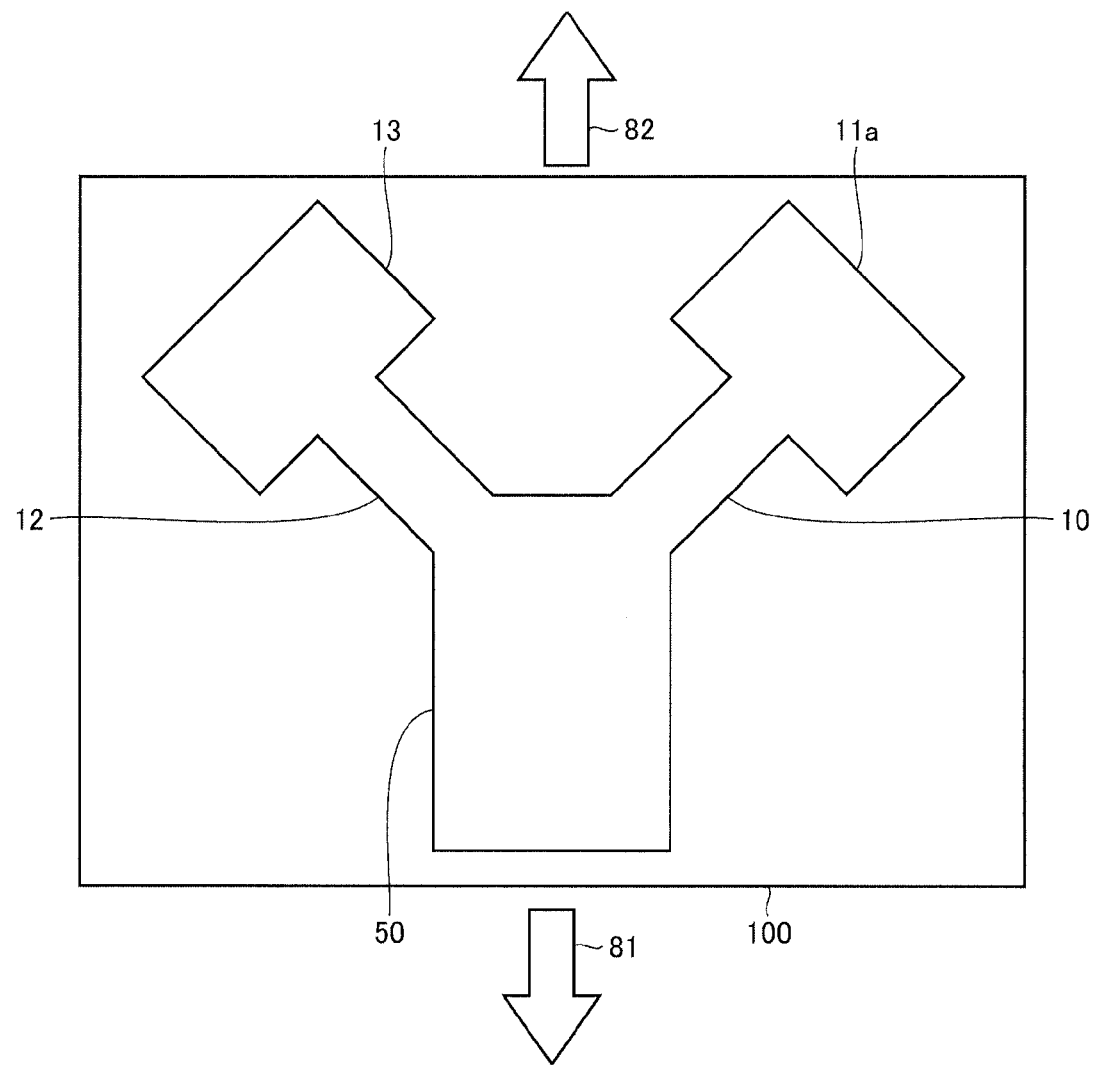
FIG. 1 is a schematic diagram representing a first embodiment of a microchip according to the present invention.

FIG. 1 is a schematic diagram viewed in plane from above of a microchip 100 according to a first embodiment of the present invention. Microchip 100 of the present invention includes a separation portion 50 separating each of a first component and a second component from a specimen containing first and second components, a first collection portion 13 collecting the first component, and a second collection portion 11a collecting the second component, a first flow path 12 guiding the first component from separation portion 50 to first collection portion 13, and a second flow path 10 guiding the second component from separation portion 50 to second collection portion 11a.

The operation of microchip 100 shown in FIG. 1 will be described hereinafter based on an example in which a specimen containing first and second components is blood. The first component is blood cells, and the second component is blood plasma having a specific gravity lower than that of the first component.

When blood is introduced to microchip 100 under the state shown in FIG. 1, the introduced blood is transferred to separation portion 50. Then, microchip 100 is rotated such that the centrifugal force is applied in the direction of arrow 81 in FIG. 1. Accordingly, the blood is separated into blood cells that are the first component and blood plasma that is the second component by application of the centrifugal force.

Then, microchip 100 under the state shown in FIG. 1 is rotated such that the centrifugal force is applied in the direction of arrow 82 in FIG. 1. At this stage, first flow path 12 and second flow path 10 each extend in a direction radiating from the center of the centrifugal force applied to the microchip (the direction including the direction of arrow 82). Therefore, the first and second components are collected at a first collection portion 13 and a second collection portion 11a through first flow path 12 and second flow path 10, respectively.

Figure 2:
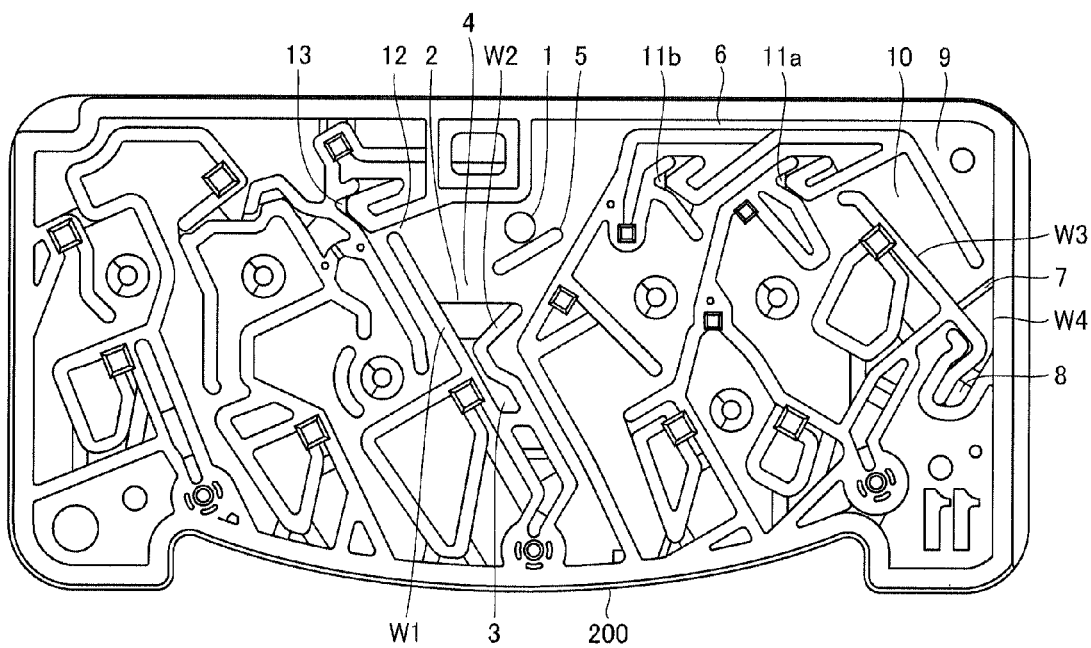
FIG. 2 is a plan view representing an example of a microchip of the present invention.

FIG. 2 is a plan view of microchip 200 that is an example of a microchip of the present invention, viewed at the top. The functional portions that will be described afterwards are incorporated into one substrate. Microchip 200 shown in FIG. 2 will be described based on an example in which a specimen containing first and second components is blood. The first component is blood cells, and the second component is blood plasma having a specific gravity lower than that of the first component.

At the most upstream portion of the fluid circuit in microchip 200, a specimen inlet 1 is provided as an opening. Below specimen inlet 1 is provided a first separation portion 3 having a first inlet 2, connected to specimen inlet 1 via a flow path 4. For the purpose of ensuring that the entire specimen properly flows into first separation portion 3 when centrifugal force is applied to cause the specimen input through specimen inlet 1 to be transferred to first separation portion 3, a flow path wall 5 is provided between specimen inlet 1 and first separation portion 3 to run along the direction from second separation portion 8 to first separation portion 3, as will be described afterwards.

First separation portion 3 is connected to third flow path 6 via first inlet 2. Third flow path 6 is connected to second separation portion 8 to via second inlet 7. In third flow path 6 of the present embodiment connecting first separation portion 3 with second separation portion 8, a fluid holding portion 9 is provided, communicating with first separation portion 3 and second separation portion 8. As shown in FIG. 2, first and second separation portions 3 and 8 are not adjacent, but spaced apart from each other. When viewed from specimen inlet 1, first and second separation portions 3 and 8 are connected, not in series, but in parallel via first and second inlets 2 and 7. A portion of third flow path 6 constitutes a portion of first flow path 12, and also a portion of second flow path 10.

Second separation portion 8 is also connected to second collection portions 11a and 11b via second flow path 10 from second inlet 7. As shown in FIG. 2, second collection portions 11a and 11b are arranged between first and second separation portions 3 and 8 such that blood plasma having a specific gravity lower than that of blood cells can be collected. Microchip 200 in FIG. 2 includes, but not limited to, two second collection portions 11a and 11b connected in series with second separation portion 8. Microchip 200 may include three or more second collection portions. Second collection portions 11a and 11b each are connected to a mixing portion not shown where a reagent and blood plasma are mixed. Second collection portions 11a and 11b also have the measuring function to measure a predetermined amount by applying centrifugal force towards the collected blood plasma in a predetermined direction and cause the collected blood plasma to partially overflow from the second collection portion. The superfluous blood plasma is stored in a waste tank not shown through a waste opening.

First separation portion 3 is connected to first collection portion 13 such that blood cells can be collected from first inlet 2 via first flow path 12. First collection portion 13 is not disposed between first and second separation portions 3 and 8 where second collection portions 11a and 11b are arranged, and is disposed at the side opposite to where second collection portions 11a and 11b are located, based on first separation portion 3. Likewise with second collection portions 11a and 11b, first collection portion 13 can measure a predetermined amount by applying centrifugal force in a predetermined direction with respect to the collected blood cells, and cause overflow from first collection portion 13. First collection portion 13 is connected to a mixing portion to have the collected blood cells mixed with a reagent. The superfluous blood cells are stored in a waste tank not shown via the waste opening.

The operation of microchip 200 of FIG. 2 will be described hereinafter with reference to FIGS. 3-8. FIGS. 3-6 represent the steps of the operation of microchip 200 shown in FIG. 2. Further, FIGS. 7 and 8 each are plan views enlarged from first separation portion 3 and second separation portion 8 in microchip 200.

(1) First Blood Plasma and Blood Cell Separation Step

Figure 3:
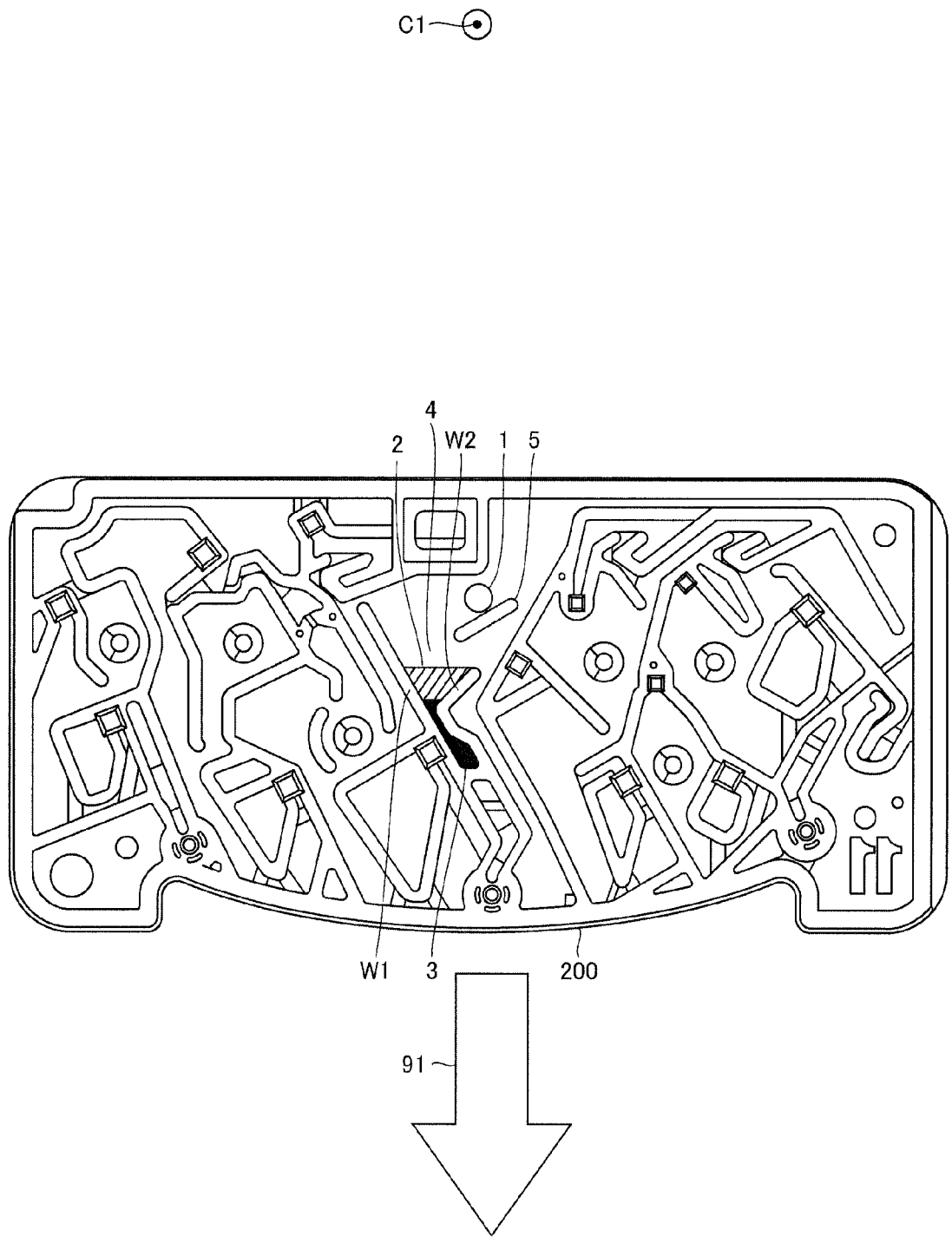
FIGS. 3-6 are diagrams showing steps of operations at the microchip of FIG. 2.

First, following introduction of the whole blood through specimen inlet 1, microchip 200 is rotated at approximately 3,000 rpm with a first centrifugal center C1 as the center, provided at the upper side in FIG. 3 (hereinafter, simply referred to as "upper side"; the same applies to FIGS. 4-6, and likewise with other directions). Accordingly, centrifugal force is applied in a downward direction 91 in FIG. 3 (hereinafter, simply referred to as "downward"; the same applies to FIGS. 4-6, and likewise with other directions). Thus, the whole blood is transferred into first separation portion 3 from first inlet 2 through flow path 4, running along flow path wall 5 from specimen inlet 1. The whole blood transferred to first separation portion 3 is divided by downward application of the centrifugal force into a blood plasma component (upper layer), and into a blood cell component (lower layer) having a larger specific gravity as compared to the blood plasma component (refer to FIGS. 3 and 7). Details of first separation portion 3 will be described afterwards.

(2) Liquid Transfer Step

Figure 4:
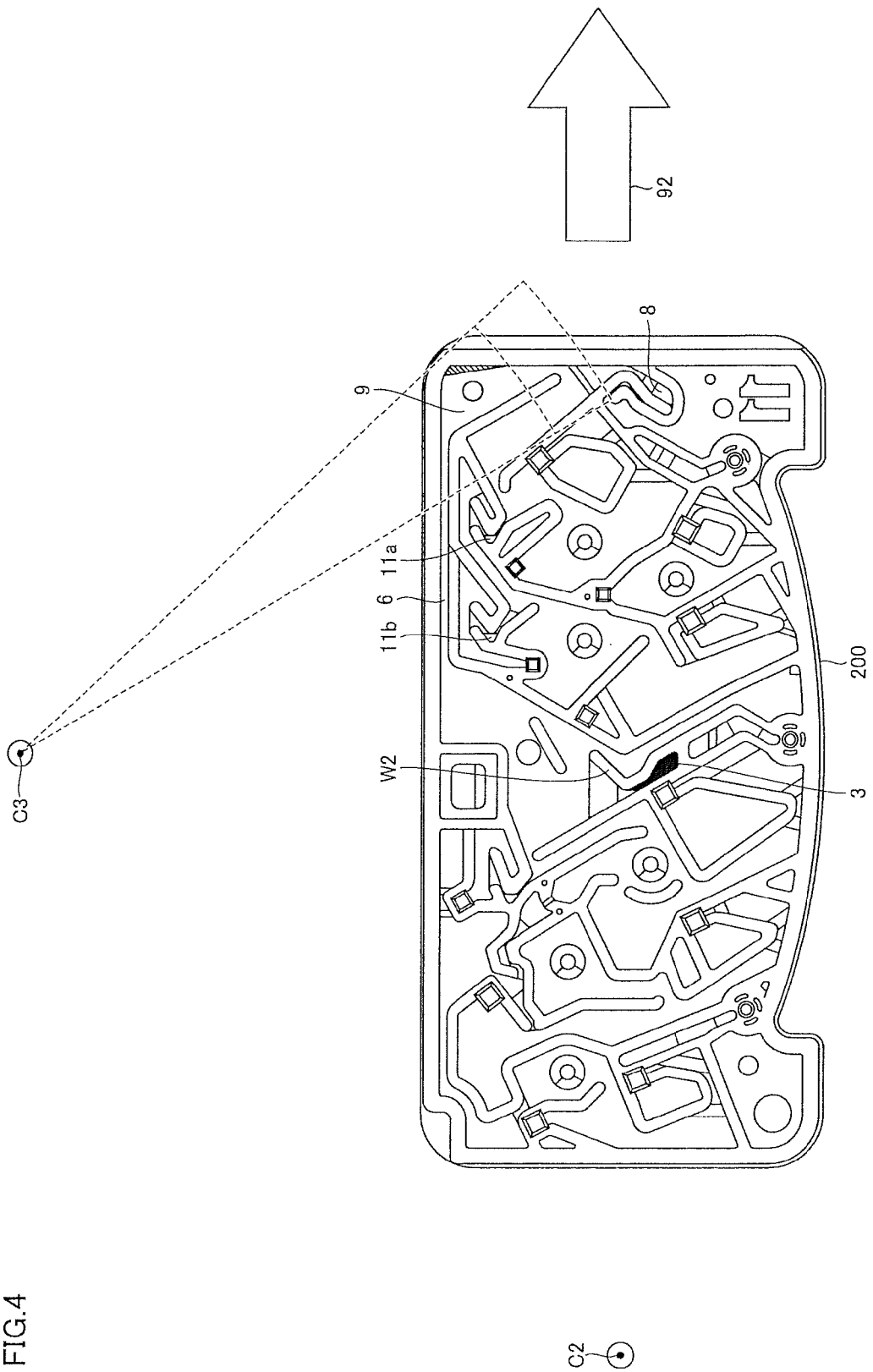

Then, by rotating microchip 200 with a second centrifugal center C2 as the center, centrifugal force is applied rightwards 92 (refer to FIG. 4). Second centrifugal center C2 is set at a site 90° or within the range of 90° counterclockwise from first centrifugal center C1, when viewed in plane from the top of the microchip. For the sake of convenience, the site corresponding to 90° counterclockwise from first centrifugal center C1 is taken as second centrifugal center C2. Second centrifugal center C2 is located at the left side of microchip 200 (refer to FIG. 4). By the application of the centrifugal force about second centrifugal center C2, the entirety of the blood plasma and a portion of blood cells in first separation portion 3 are transferred to fluid holding portion 9 through third flow path 6 to be temporarily held thereat. At first separation portion 3, a second wall face W2 that is one wall constituting first inlet 2 is formed taking a shape running along a direction from first separation portion 3 to third flow path 6 or fluid holding portion 9, or to second separation portion 8, so that the entire blood plasma component and the portion of the blood cells are transferred smoothly to second separation portion 8 through third flow path 6 and fluid holding portion 9. In the liquid transfer step, the entire blood plasma and the portion of blood cells separated in the first blood plasma and blood cell separation step are transferred to the side outer than the two concentric circles about second centrifugal center C2, where second collection portions 11a and 11b are arranged (the side farther away from second centrifugal center C2). Accordingly, collection of the blood plasma and collection of blood cells can be carried out simultaneously in the collection and measuring step that will be described afterwards.

(3) Second Blood Plasma and Blood Cell Separation Step

Figure 5:
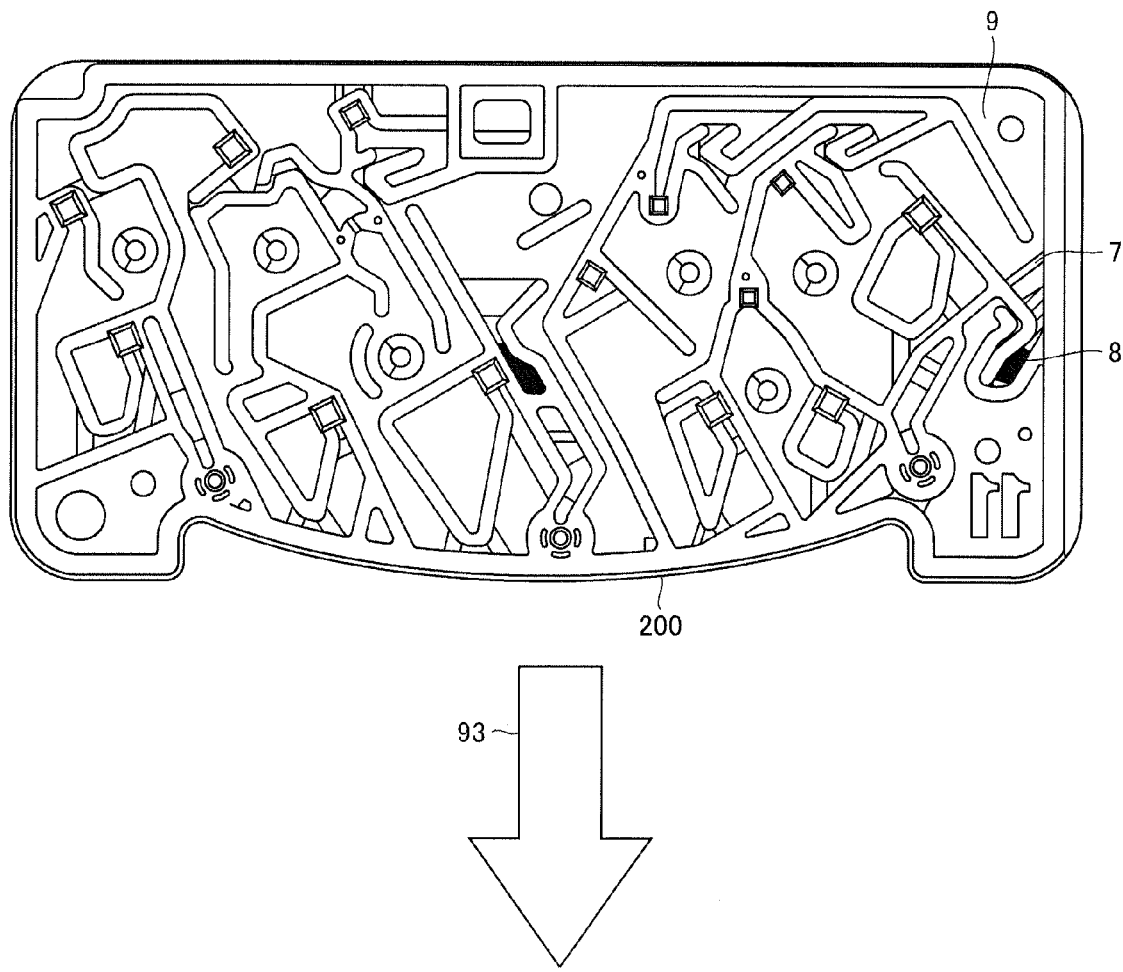

By rotating microchip 200 at approximately 3,000 rpm with a third centrifugal center C3 as the center, the centrifugal force is applied downwards 93 (refer to FIG. 5). Third centrifugal center C3 is set at a site 90° or within the range of 90° clockwise from second centrifugal center C2, when viewed in plane from the top of the microchip. For the sake of convenience, the site 90° clockwise from second centrifugal center C2 is taken as third centrifugal center C3. Third centrifugal center C3 is located at the upper side of microchip 200 (refer to FIG. 5). By applying centrifugal force about third centrifugal center C3, the entire blood plasma and the portion of the blood cells are transferred from fluid holding portion 9 to second separation portion 8 through second inlet 7, and further separated into the blood plasma component and blood cell component, likewise with the first blood plasma and blood cell separation step. Details of the structure of second separation portion 8 will be described afterwards.

(4) Collection and Measuring Step

Figure 6:
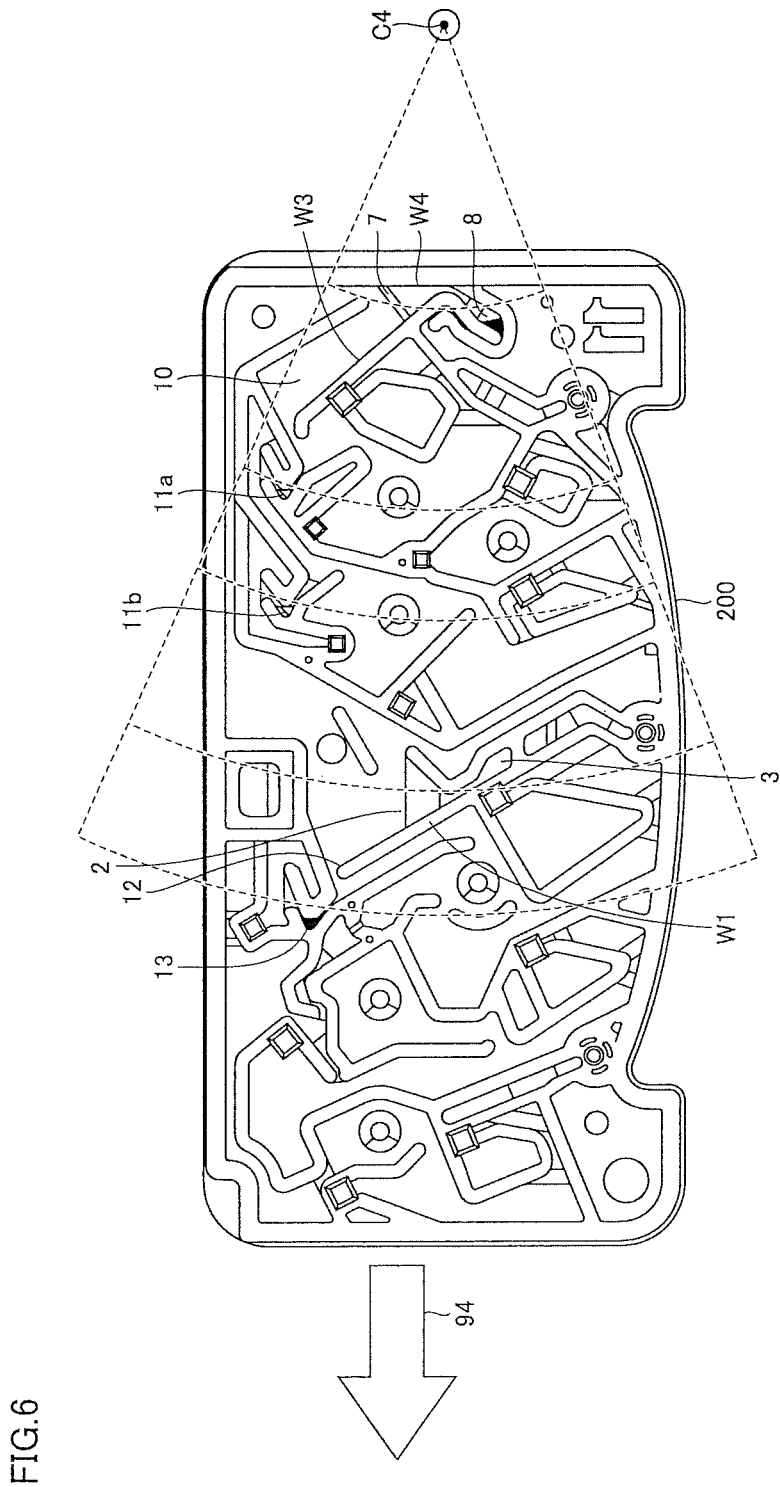

By rotating microchip 200 at approximately 3,000 rpm with a fourth centrifugal center C4 as the center, centrifugal force is applied leftwards 94 (refer to FIG. 6). Fourth centrifugal center C4 is set at a site 90° or within the range of 90° clockwise from third centrifugal center C3, when viewed in plane from the top of the microchip. For the sake of convenience, the sites 90° clockwise from third centrifugal center C3 is taken as fourth centrifugal center C4. Fourth centrifugal center C4 is located at the right side of microchip 200 (refer to FIG. 6). By applying centrifugal force about fourth centrifugal center C4, only the blood plasma that is the supernatant solution is transferred through second inlet 7 of second separation portion 8 to second collection portion 11a via second flow path 10. Moreover, second collection portion 11a is configured to measure a predetermined amount, allowing measuring of the predetermined amount. Application of centrifugal force to the collected blood plasma causes overflow of the plasma exceeding the amount. The overflowing blood plasma is transferred to second collection portion 11b connected in series with second collection portion 11a to be measured in a similar manner. The superfluous portion is transferred to a waste tank not shown through a waste outlet. At second separation portion 8, a third wall face W3 that is one wall constituting second inlet 7 is formed taking a shape running along a direction from second separation portion 8 to second collection portion 11a such that blood plasma is transferred smoothly to second collection portion 11a. The other fourth wall face W4 constituting second inlet 7 is formed running along a direction from second separation portion 8 towards fluid holding portion 9.

By the application of centrifugal force leftwards 94 in the present step, only the blood cells remaining in first separation portion 3 are transferred from first inlet 2 of first separation portion 3 to first collection portion 13 via first flow path 12, simultaneous to the collection and measuring of blood plasma at second collection portions 11a and 11b described above. First collection portion 13 is configured to also measure a predetermined amount, similar to second collection portions 11a and 11b, and can measure a predetermined amount by causing overflow from first collection portion 13. The superfluous overflow is transferred to a waste tank not shown through a waste outlet, similar to second collection portions 11a and 11b. At first separation portion 3, first wall face W1 constituting one of the walls of first inlet 2 is formed taking a shape running along a direction from first separation portion 3 to first collection portion 13 such that blood cells can be smoothly transferred to first collection portion 13.

(5) Mixing Step

The blood plasma and blood cells collected at each collection portion are mixed with a prescribed reagent at a mixing portion for reaction. By providing a plurality of second collection portions and causing one to have a non-reactive reagent that does not react with blood plasma and the like to be mixed, a measurement of comparison to a substance mixed with a reactive reagent can be achieved.

First flow path 12 uniting first separation portion 3 and first collection portion 13 and second flow path 10 uniting second separation portion 8 and second collection portion 11a are both arranged in a radiating direction from fourth centrifugal center C4. This arrangement allows first and second components to be collected simultaneously from each separation portion when the microchip is rotated about fourth centrifugal center C4.

As shown in FIG. 6, second separation portion 8, second collection portions 11a and 11b, first separation portion 3, and first collection portion 13 are arranged in the cited order on concentric circles differing in the direction radiating from fourth centrifugal center C4. In order to transfer only the blood plasma (supernatant solution) having a specific gravity lower than that of the blood cells separated at second separation portion 8 in the above-described second blood plasma and blood cell separation step to second collection portions 11a and 11b from second separation portion 8 by means of centrifugal force in the next collection and measuring step, second collection portion 11a is provided on a concentric circle having a radius larger than that of the concentric circle about fourth centrifugal center C4 where second separation portion 8 is located. This arrangement of second collection portions 11a and 11b between first separation portion 3 and second separation portion 8 allows the collection of blood plasma alone.

In order to transfer the blood cells left in first separation portion 3 in the first blood plasma and blood cell separation step to first collection portion 13 by means of centrifugal force, simultaneous to the transfer of blood plasma from second separation portion 8 to second collection portion 11a, first collection portion 13 is provided on a concentric circle having a radius larger than that of the concentric circle about fourth centrifugal center C4 where first separation portion 3 is located. Accordingly, the blood cells and blood plasma can be transferred to first collection portion 13 and second collection portion 11a, respectively, at the same time in the above-described collection and measuring step. Therefore, the blood plasma and blood cells can be mixed with individual reagents for reaction simultaneously by the process set forth above even though unseparated blood is introduced through only one specimen inlet 1. Then, respective mixed liquids can be transferred to the detection portion to allow detection of HbAlc in the blood cells and glucose in the blood plasma, for example, at the same time.

In the liquid transfer step set forth above, centrifugal force is applied about second centrifugal center C2 in order to leave a predetermined amount of blood cells in first separation portion 3. Moreover, second separation portion 8, second collection portions 11a and 11b, first separation portion 3, and first collection portion 13 are arranged in the cited order on concentric circles differing in the direction radiating from fourth centrifugal center C4 located at the side opposite to second centrifugal center C2 with the microchip therebetween, in order to ensure transfer of the entire blood plasma and the portion of blood cells to second separation portion 8. In addition, to further ensure liquid transfer, second wall face W2 constituting second inlet 7 of second separation portion 8 is formed running along the direction from first separation portion 3 to second separation portion 8 or third flow path 6.

Further, as shown in FIG. 2, a first wall face W1 constituting first inlet 2 is formed running along a direction from first separation portion 3 to first collection portion 13, and a third wall face W3 of second inlet 7 is formed running along a direction from second separation portion 8 to second collection portion 11a. This is to ensure the transfer from first separation portion 3 to first collection portion 13, and from second separation portion 8 to second collection portion 11a in the collection and measuring step.

Fluid holding portion 9 and second separation portion 8 are arranged on different concentric circles about third centrifugal center C3. The radius of the concentric circle where second separation portion 8 is arranged is set larger than the radius of the concentric circle where fluid holding portion 9 is arranged (refer to FIG. 4). During the fluid transfer step set forth above, the entire blood plasma and a portion of blood cells can be held at the relevant holding portion when the centrifugal force is applied, as shown in FIG. 4. Further in the subsequent second blood plasma and blood cell separation step, the liquid can be transferred from fluid holding portion 9 to second separation portion 8 through second inlet 7, as shown in FIG. 5.

Figure 7:
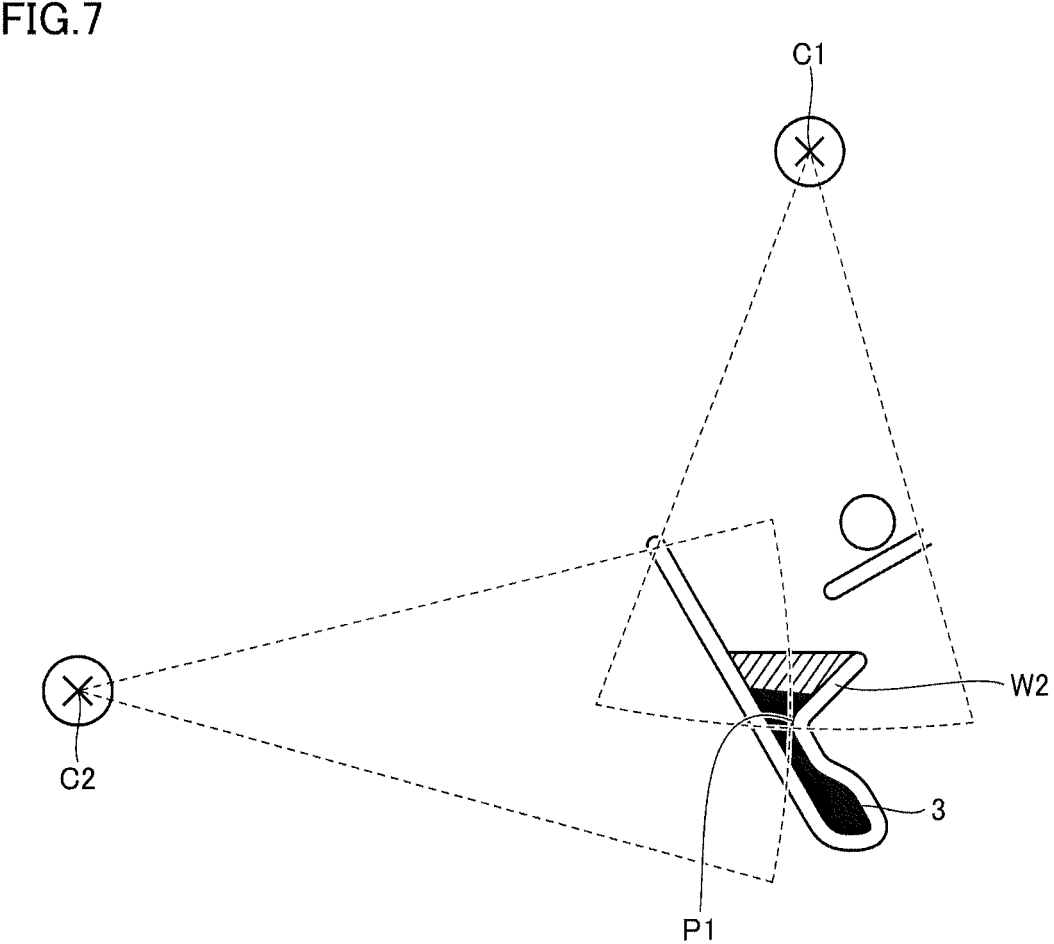
FIG. 7 is an enlarged plan view of a first separation portion in the microchip of FIG. 2.

The details of the first separation portion will be described hereinafter with reference to FIG. 7 that is an enlarged view of first separation portion 3 of microchip 200 shown in FIG. 2. First separation portion 3 shown in FIG. 7 is L-shaped (may take an inverted L shape in consideration of arrangement conditions). A vertex P1 of the L shape is arranged such that the boundary between the blood plasma and blood cells is located at a circumference of a concentric circle about first centrifugal center C1, inner than the circle about first centrifugal center C1 passing through the contacting point of the liquid level of the whole blood obtained by the liquid transfer step set forth above and the vertex (vertex P1 of the L shape) of second wall face W2 that is the inner wall closer to first centrifugal center C1, when centrifugal force is applied in the first blood plasma and blood cell separation step. Accordingly, the entire blood plasma and a portion of blood cells can be transferred from first separation portion 3 during the liquid transfer step to leave only the blood cells in first separation portion 3. Therefore, only the blood cells can be transferred from first separation portion 3 to first collection portion 13 in the collection and measuring step.

Figure 8:
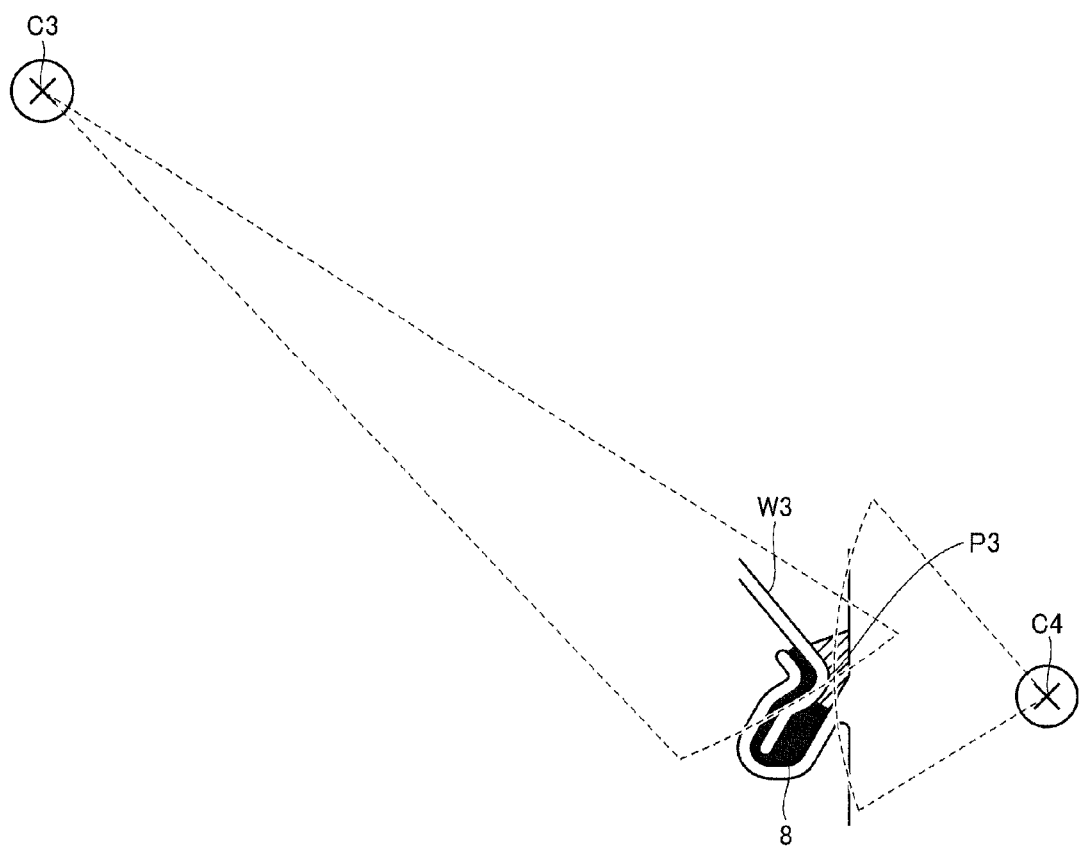
FIG. 8 is an enlarged plan view of a second separation portion in the microchip of FIG. 2.

The details of the second separation portion will be described hereinafter with reference to FIG. 8 showing an enlarged view of second separation portion 8 in microchip 200 of FIG. 2. Second separation portion 8 shown in FIG. 8 takes an inversed L shape (may take an L shape in consideration of arrangement conditions). A vertex P3 of the inversed L shape is arranged such that the boundary between the blood plasma and blood cells is located at an outer circumferential side of a circle about third centrifugal center C3 passing through the contacting point of the liquid level of the entire blood plasma and a portion of blood cells obtained by the collection and weighing step and the vertex (vertex P3 of the inversed L shape) of third wall face W3 that is the inner wall closer to third centrifugal center C3. Accordingly, only the blood plasma can be transferred from second separation portion 8 in the collection and measuring step mode, allowing collection at second collection portion 11a.

(Second Embodiment)

Figure 9:
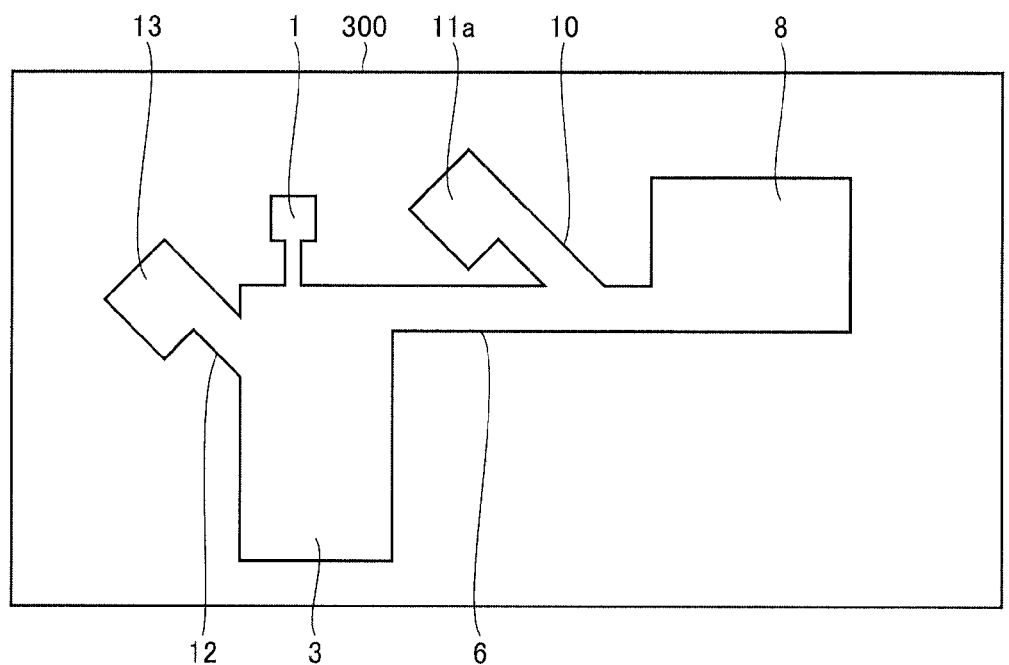
FIG. 9 is a schematic diagram representing a second embodiment of a microchip according to the present invention.

FIG. 9 is a schematic plan view of a microchip 300 according to a second embodiment of the present invention. Microchip 300 includes a first separation portion 3 separating at least a portion of a first component from a specimen containing first and second components, a second separation portion 8 separating at least a portion of the second component from the specimen containing first and second components, a third flow path 6 guiding a portion of the first component and the second component of the specimen from first separation portion 3 to second separation portion 8, a first collection portion 13, a second collection portion 11a, a first flow path 12 guiding the first component from first separation portion 3 to first collection portion 13, and a second flow path 10 guiding the second component from second separation portion 8 to second collection portion 11a. Microchip 300 is configured to obtain the first component by separating the first component from first separation portion 3 and the second component by separating the second component from the second separation portion. As shown in FIG. 9, first flow path 12 guiding the first component from first separation portion 3 to first collection portion 13 and second flow path 10 guiding the second component from second separation portion 8 to second collection portion 11a are both formed to run in the same direction relative to the direction of the centrifugal force applied in the collection and measuring step. Such a configuration allows simultaneous collection of first and second components separated in the collection and measuring step set forth above.

Although the above description is based on a fluid constituted of two components having different specific gravities such as blood plasma and blood cells, the microchip of the present invention is also applicable to a fluid constituted of two or more components having different properties such as the hydrophilic property and hydrophobic property. In this case, the centrifugal force does not have to be intentionally applied for separation since separation is effected by the hydrophilic property and hydrophobic property itself. However, measurement will be allowed of a fluid having two or more components separated into two or more layers, each collected by a predetermined amount and made to react with a reaction agent or the like to detect a property corresponding to the reaction.

The material of the substrate constituting the microchip of the present invention is not particularly limited. For example, organic materials such polyethylene terephthalate (PET), polybutyrene terephthalate (PBT), polymethyl methacrylate (PMMA), polycarbonate (PC), polystyrene (PS), polypropylene (PP), polyethylene (PE), polyethylene naphthalate (PEN), poly arylate resin (PAR), acrylonitrile-butadiene-styrene resin (ABS), polyvinyl chloride resin (PVC), polymethylpentene resin (PMP), polybutadiene resin (PBD), biodegradable polymer (BP), cycloolefin polymer (COP), polydimethylsiloxane (PDMS); as well as inorganic materials such as silicon, glass and quartz may employed.

The method of forming a groove constituting a fluid circuit at the surface of the substrate is not particularly limited. Injection molding using a mold having a transfer structure, imprinting method, and the like can be cited. In the case where the substrate is formed based on an inorganic material, etching and the like may be employed.

Although the present invention has been described and illustrated in detail, it is clearly understood that the same is by way of illustration and example only and is not to be taken by way of limitation, the scope of the present invention being interpreted by the terms of the appended claims.

What is claimed is:

1. A microchip comprising:
   a separation portion separating each of a first component and a second component from a specimen containing first and second components,
   a first collection portion collecting said first component,
   a second collection portion collecting said second component,
   a first flow path guiding said first component from said separation portion to said first collection portion, and
   a second flow path guiding said second component from said separation portion to said second collection portion,
   wherein the first collection portion is configured to measure a predetermined amount of the first component therein and the second collection portion is configured to measure a predetermined amount of the second component therein by causing a partial overflow of the first component and the second component introduced in the respective collection portions, wherein the microchip is arranged so that the first and second collection portions are filled at the same time by application of a centrifugal force.

2. The microchip according to claim 1, wherein each of said first flow path and said second flow path extends in a direction radiating from the center of centrifugal force applied to said microchip.

3. The microchip according to claim 1, wherein
   said separation portion comprises a first separation portion separating at least a portion of said first component from the specimen, a second separation portion separating at least a portion of said second component from the specimen, and a third flow path guiding a portion of the first component and the second component of the specimen from said first separation portion to said second separation portion, and
   said first flow path is located between said first separation portion and said first collection portion, and said second flow path is located between said second separation portion and said second collection portion.

4. The microchip according to claim 3, wherein said first flow path and said third flow path are partially shared.

5. The microchip according to claim 3, wherein said second flow path and said third flow path are partially shared.

6. A microchip comprising:
   a first separation portion separating at least a portion of a first component from a specimen containing first and second components,
   a second separation portion separating at least a portion of the second component from the specimen containing first and second components, and
   a flow path guiding a portion of the first component and the second component of the specimen from said first separation portion to said second separation portion,
   said first component being obtained by separating said first component from said first separation portion, and said second component being obtained by separating said second component from said second separation portion,
   a first collection portion collecting the first component, and a second collection portion collecting the second component,
   a first flow path guiding the first component from the first separation portion to the first collection portion, and a second flow path guiding the second component from the second separation portion to the second collection portion,
   wherein the first collection portion is configured to measure a predetermined amount of the first component therein and the second collection portion is configured to measure a predetermined amount of the second component therein by causing a partial overflow of the first component and the second component introduced in the respective collection portions, wherein the microchip is arranged so that the first and second collection portions are filled at the same time by application of a centrifugal force.

7. The microchip according to claim 6, wherein each of said first flow path and said second flow path extends in a direction radiating from the center of centrifugal force applied to said microchip.

8. The microchip according to claim 6, wherein said second separation portion, said second collection portion, said first separation portion, and said first collection portion are arranged in the cited order on concentric circles differing in the direction radiating from the center of centrifugal force applied to said microchip.

* * * * *